United States Patent
Milne et al.

(10) Patent No.: US 11,413,418 B2
(45) Date of Patent: Aug. 16, 2022

(54) DRYING EXPIRATORY LIMB WITH TAILORED TEMPERATURE PROFILE AND MULTI-LUMEN CONFIGURATION

(71) Applicant: Fisher & Paykel Healthcare Limited, Auckland (NZ)

(72) Inventors: Robert Andrew David Milne, Auckland (NZ); Timothy Dee Gierke, Wilmington, DE (US)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 16/668,653

(22) Filed: Oct. 30, 2019

(65) Prior Publication Data

US 2020/0121882 A1    Apr. 23, 2020

Related U.S. Application Data

(63) Continuation of application No. 14/777,440, filed as application No. PCT/NZ2014/000038 on Mar. 14, 2014, now Pat. No. 10,500,364.
(Continued)

(51) Int. Cl.
   *A61M 16/00*    (2006.01)
   *A61M 16/08*    (2006.01)
   (Continued)

(52) U.S. Cl.
   CPC .... *A61M 16/0808* (2013.01); *A61M 16/0875* (2013.01); *A61M 16/0883* (2014.02);
   (Continued)

(58) Field of Classification Search
   CPC .......... A61M 16/0808; A61M 16/0875; A61M 16/0883; A61M 16/1095; A61M 16/161;
   (Continued)

(56) References Cited

U.S. PATENT DOCUMENTS

| 4,265,235 A | 5/1981 | Fukunaga |
| 4,698,890 A | 10/1987 | Neaves |

(Continued)

FOREIGN PATENT DOCUMENTS

| EP | 0535379 | 10/1996 |
| GB | 2142376 | 7/1984 |

(Continued)

OTHER PUBLICATIONS

U.S. Appl. No. 14/777,438, filed Sep. 15, 2015, Milne.
(Continued)

*Primary Examiner* — Steven O Douglas

(74) *Attorney, Agent, or Firm* — Knobbe Martens Olson & Bear LLP

(57) ABSTRACT

A drying expiratory limb of a breathing circuit is provided that is configured to increase or optimize drying of a gas to reduce or prevent condensation. The drying expiratory limb can include a wall that is at least partly made of a breathable material configured to allow transmission of water vapor but substantially prevent transmission of liquid water. The wall includes first and second openings in the wall, the openings respectively configured to receive a gas at a first temperature and a first relative humidity and to allow the gas to exit having a second temperature and a second relative humidity. The drying expiratory limb can be configured to tailor the temperature drop of the gas along the wall to maintain a relative humidity within a targeted range and/or to maintain the gas temperature above its dew point temperature.

23 Claims, 9 Drawing Sheets

Related U.S. Application Data

(60) Provisional application No. 61/790,424, filed on Mar. 15, 2013, provisional application No. 61/789,754, filed on Mar. 15, 2013.

(51) Int. Cl.
  *A61M 16/10* (2006.01)
  *A61M 16/16* (2006.01)

(52) U.S. Cl.
  CPC ...... *A61M 16/1095* (2014.02); *A61M 16/161* (2014.02); *A61M 16/16* (2013.01); *A61M 2205/0238* (2013.01); *A61M 2205/33* (2013.01); *A61M 2205/3368* (2013.01); *A61M 2205/3633* (2013.01); *A61M 2205/3673* (2013.01); *A61M 2205/50* (2013.01)

(58) Field of Classification Search
  CPC .......... A61M 16/16; A61M 2205/0238; A61M 2205/33; A61M 2205/3368; A61M 2205/3633; A61M 2205/3673; A61M 2205/50
  See application file for complete search history.

(56) References Cited

U.S. PATENT DOCUMENTS

| | | | |
|---|---|---|---|
| 4,727,871 | A | 3/1988 | Smargiassi et al. |
| 5,015,013 | A | 5/1991 | Nadin |
| 5,079,802 | A | 1/1992 | Blasé et al. |
| 5,188,609 | A | 2/1993 | Bayless et al. |
| 5,233,996 | A | 8/1993 | Coleman et al. |
| 5,284,160 | A | 2/1994 | Dryden |
| 5,454,061 | A | 9/1995 | Carlson |
| 5,501,212 | A | 3/1996 | Psaros |
| 5,614,588 | A | 3/1997 | Steenblock |
| 5,983,896 | A | 11/1999 | Fukunaga et al. |
| 6,078,730 | A | 6/2000 | Huddart et al. |
| 6,513,767 | B1 | 2/2003 | Rodgers |
| 6,568,716 | B1 | 5/2003 | Fleber |
| 6,769,431 | B2 | 8/2004 | Smith et al. |
| 6,854,694 | B1 | 2/2005 | Van Etten |
| 7,140,366 | B2 | 11/2006 | Smith et al. |
| 7,146,979 | B2 | 12/2006 | Seakins et al. |
| 7,382,531 | B2 | 6/2008 | Tsuchiya et al. |
| 9,032,952 | B2 | 5/2015 | Grilliot et al. |
| 9,602,020 | B2 | 3/2017 | Kondo et al. |
| 10,500,364 | B2 | 12/2019 | Milne et al. |
| 10,532,177 | B2 | 1/2020 | Hermez et al. |
| 10,688,268 | B2 | 6/2020 | Gulliver et al. |
| 2003/0005554 | A1 | 1/2003 | Nagayasu |
| 2004/0099268 | A1 | 5/2004 | Smith et al. |
| 2012/0125333 | A1 | 5/2012 | Bedford et al. |

FOREIGN PATENT DOCUMENTS

| | | |
|---|---|---|
| GB | 2139110 | 11/1984 |
| GB | 2252515 | 8/1992 |
| JP | 2000-024111 | 1/2000 |
| WO | WO 2004/105847 | 12/2004 |
| WO | WO 2010/131189 | 11/2010 |
| WO | WO 2011/077250 | 6/2011 |
| WO | WO 2011/149362 | 12/2011 |
| WO | WO 2011/162622 | 12/2011 |

OTHER PUBLICATIONS

International Search Report and Written Opinion dated May 9, 2014 for PCT Application No. PCT/NZ2014/000038 filed Mar. 14, 2014.
International Search Report dated Jul. 15, 2014 for PCT Application No. PCT/NZ2014/000039 filed Mar. 14, 2014.
International Preliminary Report on Patentability dated Sep. 15, 2015 for International Application No. PCT/NZ2014/000039.
Claim Construction Order in the United States District Court of the Central District of California (Case No. 8:19-cv-00835-JVS-DFM) dated Mar. 27, 2020.
Quisona—A clip with opposing sprung jaws, the jaws are intended for clipping to a bed sheet, the inner of the clip collar is provided for locating of a tube.

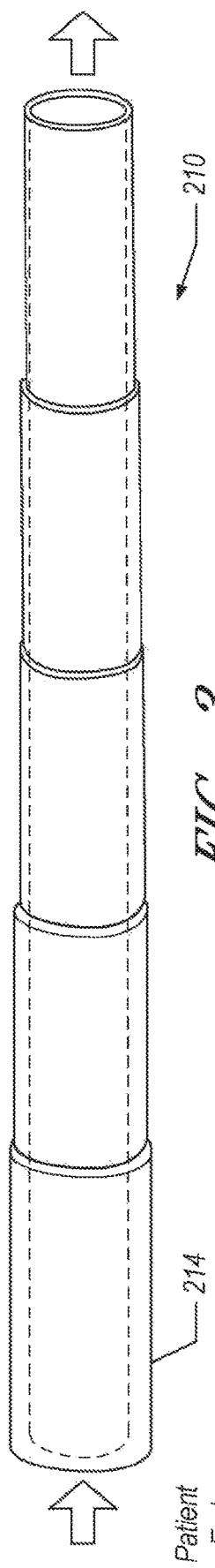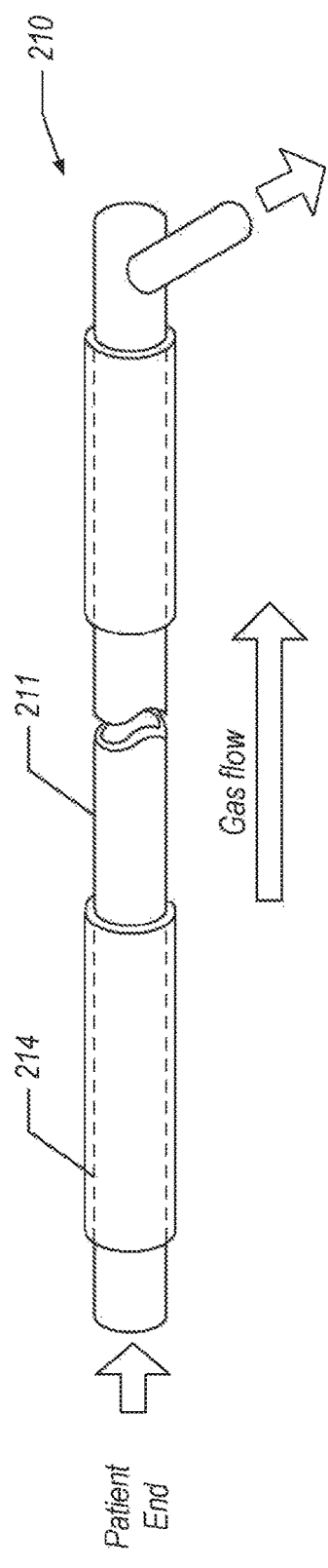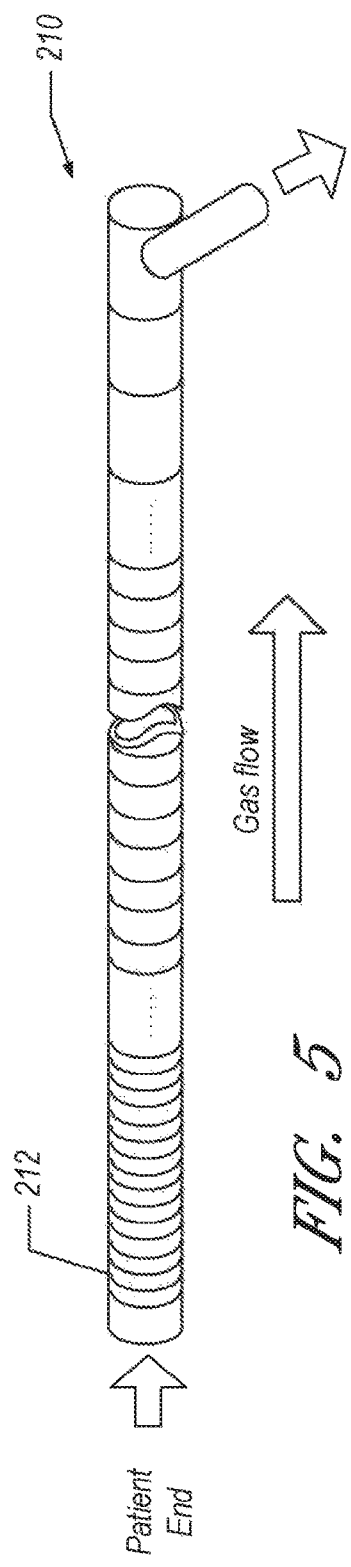

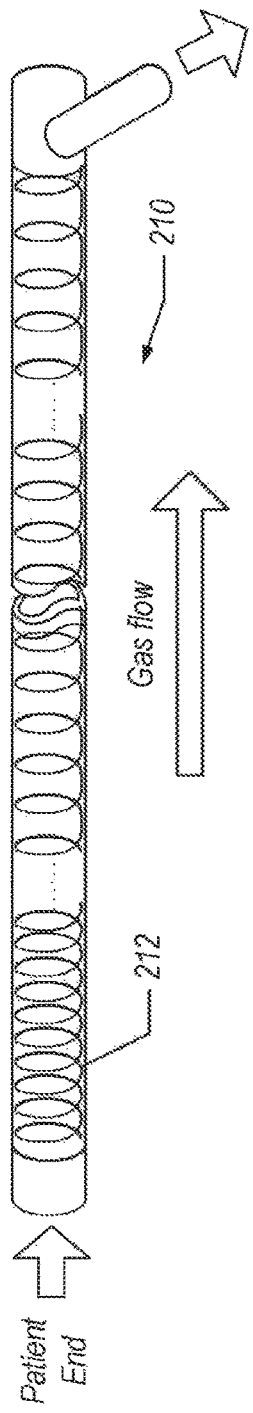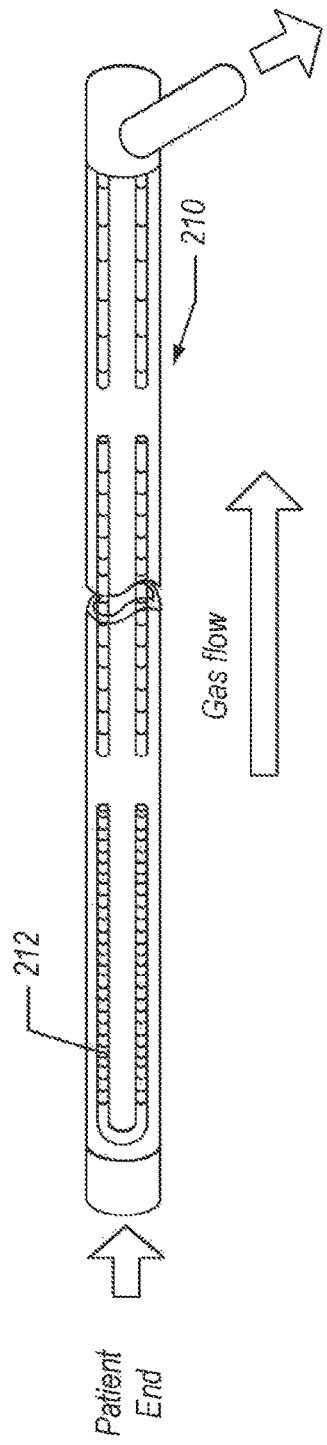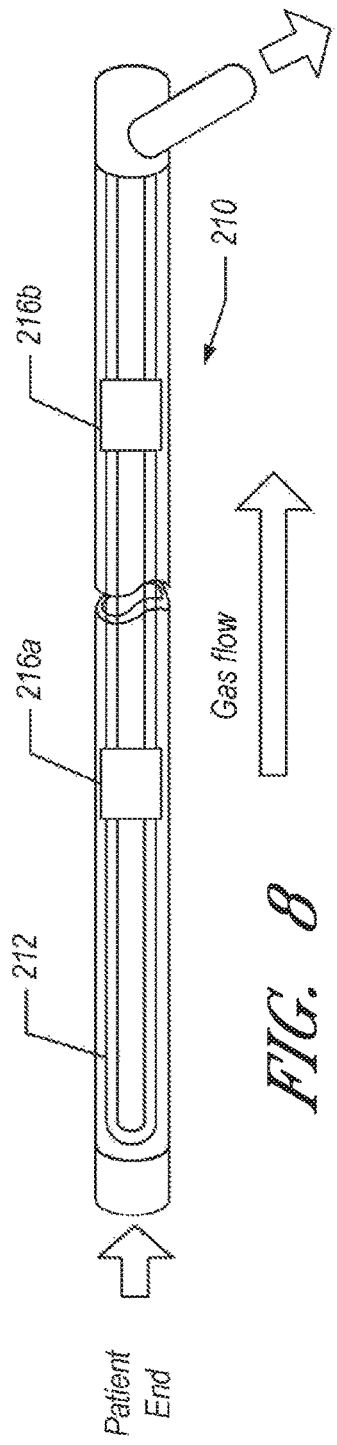

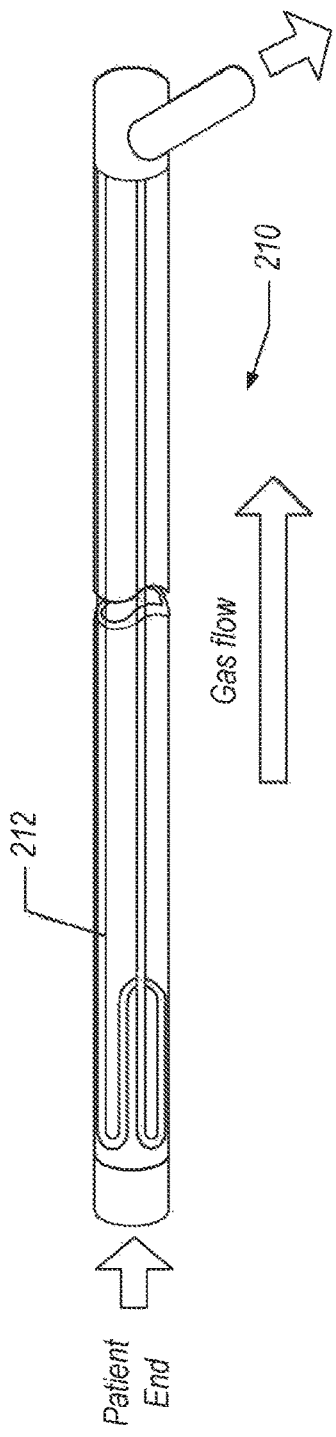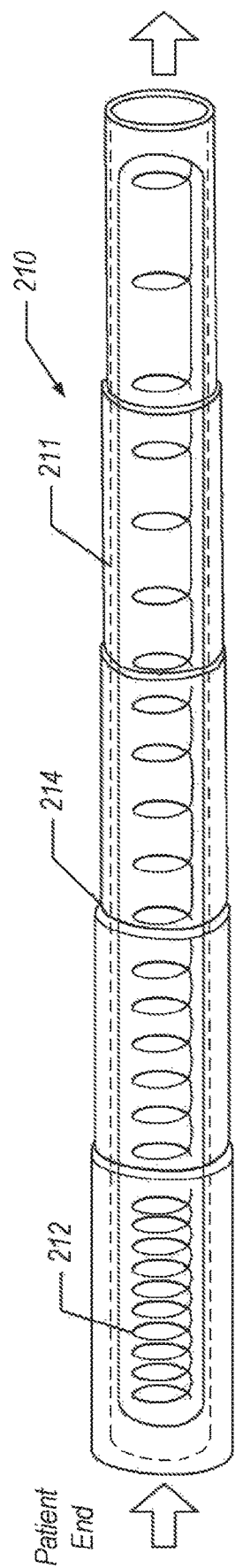

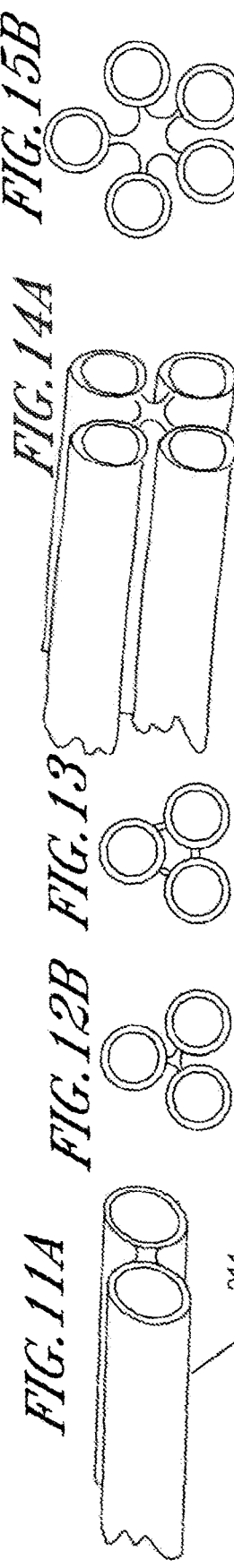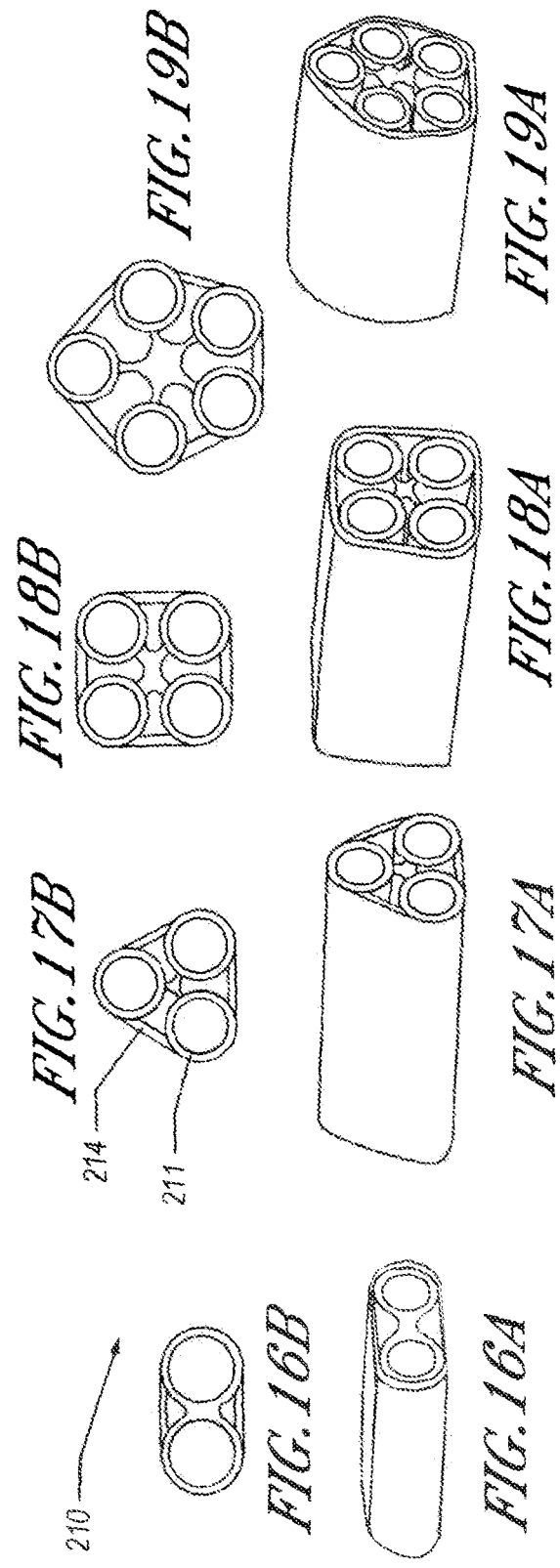

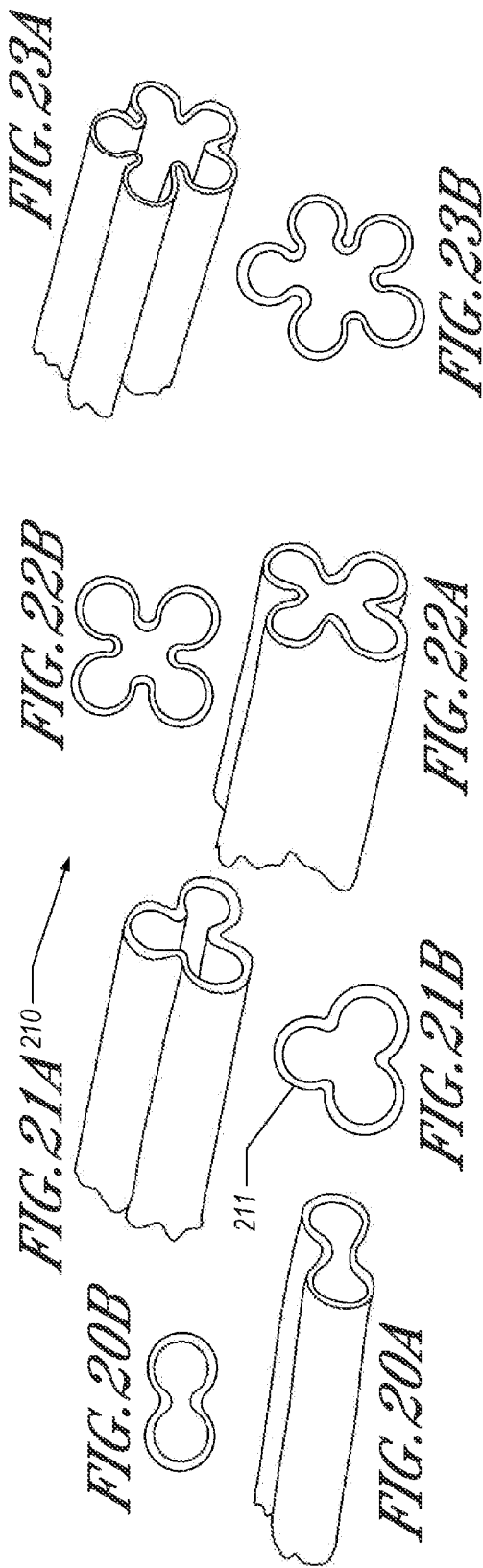

DRYING EXPIRATORY LIMB WITH TAILORED TEMPERATURE PROFILE AND MULTI-LUMEN CONFIGURATION

CROSS-REFERENCE TO RELATED APPLICATIONS

This application is a continuation of U.S. patent application Ser. No. 14/777,440, entitled "DRYING EXPIRATORY LIMB WITH TAILORED TEMPERATURE PROFILE AND MULTI-LUMEN CONFIGURATION," filed Sep. 15, 2015, which is a national stage application of PCT Application No. PCT/NZ2014/000038, entitled "DRYING EXPIRATORY LIMB WITH TAILORED TEMPERATURE PROFILE AND MULTI-LUMEN CONFIGURATION," filed Mar. 14, 2014, which claims the benefit of U.S. Provisional Application No. 61/790,424, entitled "DRYING EXPIRATORY LIMB WITH TAILORED TEMPERATURE PROFILE," filed Mar. 15, 2013, and U.S. Provisional Application No. 61/789,754, entitled "DRYING EXPIRATORY LIMB WITH TAILORED TEMPERATURE PROFILE AND MULTI-LUMEN CONFIGURATION," filed Mar. 15, 2013, each of which is incorporated by reference herein in its entirety.

BACKGROUND

Field

This disclosure relates generally to expiratory limbs for use in respiratory circuits, and in particular to a breathing circuit with an improved drying expiratory limb configured to provide improved drying performance by providing a tailored temperature profile along the tube.

Description of Related Art

In medical applications, various components transport gases having high levels of relative humidity to and from patients. Condensation, or "rain out," can be a problem when the high humidity gases come into contact with the walls of a component at a lower temperature. However, condensation is dependent on many factors, including not only the temperature profile in the component, but also the gas flow rate, component geometry, and the intrinsic "breathability" of the material used to form the component, that is the ability of the material to transmit water vapor, while substantially resisting the bulk flow of liquid water and the bulk flow of gas.

For example, PAP systems (ventilation systems that provide patients with breathing gases at positive pressure) use breathing tubes for delivering and removing inspiratory and expiratory gases. In these applications, and in other breathing applications such as assisted breathing, the gases inhaled by a patient are usually delivered through an inspiratory limb at humidity near saturation. The breathing gases exhaled by a patient flow through an expiratory limb and are usually fully saturated. Condensation may form on the interior walls of a breathing circuit component during patient inhalation, and significant condensation levels may form during patient exhalation. In addition, condensation may occur where the exhaled gases enter the ventilator. Such condensation is particularly deleterious when it is in close proximity to the patient. For instance, mobile condensate forming in a breathing limb (either inspiratory or expiratory) can be breathed or inhaled by a patient and may lead to coughing fits or other discomfort.

Many gas humidification systems deliver heated and humidified gases for various medical procedures, including respiratory treatment, laparoscopy, and the like. These systems can be configured to control temperature, humidity and flow rates through the use of sensors. To reduce or avoid condensation or rain out, a breathing circuit can have heaters associated with gas conduits where the heaters provide heat to the gas as it flows to and/or from the user. The conduit heaters can be controlled to provide heat to the gas so that the gas maintains a suitable temperature and/or humidity.

SUMMARY

The systems, methods and devices described herein have innovative aspects, no single one of which is indispensable or solely responsible for their desirable attributes. Without limiting the scope of the claims, some of the advantageous features will now be summarized.

In general, an expiratory limb is configured to dry a gas as it passes through the expiratory limb prior to reaching a ventilator. The expiratory limb can be configured to dry the gas sufficiently to reduce or eliminate condensation in the ventilator. Drying can be limited at least in part by a surface area of the tube and/or a residence time of the gas in the expiratory limb. Increasing the surface area of the expiratory limb can increase drying, but it can also increase heat loss, which can lead to rain out. It may be advantageous, then, to provide a drying expiratory limb that provides a tailored temperature profile of the gas along the expiratory limb to increase drying, to reduce or prevent rain out along the tube, and/or to reduce or prevent condensation in the ventilator. In some embodiments, an improved or optimized drying of the gas within a drying expiratory limb is accomplished by controlling the temperature of the gas as it passes along the drying expiratory limb to maintain a difference between the gas temperature and its dew point temperature approximately constant. In some embodiments, this temperature difference is less than about 2° C., less than about 1.5° C., or between about 0.9° C. and about 1° C. In some embodiments, an improved or optimized drying of the gas within the drying expiratory limb is accomplished by keeping the relative humidity of the gas between about 90% and about 99%, between about 95% and about 99%, or between about 95% and about 97%. In some embodiments, this may be accomplished by keeping the dew point temperature and absolute humidity approximately linear along the length of the expiratory limb. In some embodiments, the temperature drop of the gas from the beginning of the tube to about the first 300 mm or 400 mm of the drying expiratory limb is less than −0.01° C./mm or between 0° C./mm and about −0.009° C./mm and the total temperature drop across the expiratory limb length is less than about 10° C., or between about 3° C. and about 10° C. Accordingly, the drying expiratory limbs and temperature control mechanisms disclosed herein can be configured to tailor a temperature profile of the gas to increase or optimize drying of the gas, to reduce or eliminate rain out in the tube, and/or to reduce or eliminate condensation in the ventilator. In some embodiments, a drying expiratory limb is disclosed that provides an optimal drying of a gas where the optimal drying is where no condensation occurs in the tube or in the ventilator through a tailored temperature control process.

Some embodiments provide for a drying expiratory limb for use in a respiratory circuit which can include a wall having a first end and a second end separated by an expiratory limb length. The wall defines a space within and at least a part of said wall comprises a breathable material configured to allow transmission of water vapor but substantially prevent transmission of liquid water. The drying expiratory limb includes a first opening in the first end of the wall, the first opening configured to receive a gas at a first temperature and a first relative humidity. The drying expiratory limb includes a second opening in the second end of the wall configured to allow the gas to exit the drying expiratory limb, the gas having a second temperature and a second relative humidity upon exiting the drying expiratory limb. The drying expiratory limb is configured such that a difference between a temperature of the gas and a dew point temperature of the gas along the drying expiratory limb length is approximately constant.

In some aspects of the embodiment, the drying expiratory limb further includes an insulating material attached to an outer surface of the wall. The insulating material can be configured to control the temperature drop of the gas to increase drying of the gas along the expiratory limb length. In some embodiments, an amount of the insulating material is substantially constant along the expiratory limb length. The amount of the insulating material can vary along the expiratory limb length.

In some aspects, the drying expiratory limb can include a heater wire configured to selectively receive electrical power to provide heat to the gas in the drying expiratory limb. In some aspects, the heater wire is configured to control the temperature drop of the gas to increase drying of the gas along the expiratory limb length. In a further aspect, the drying expiratory limb includes two or more heaters that are configured to control the temperature of the gas to be above the dew point temperature by a targeted amount. In another aspect, the heater wire has a varying pitch spacing along the expiratory limb length, and, in some implementations, the pitch spacing increases with distance from the first end. In some implementations, the heater wire comprises at least two sections, the two sections being configured to be independently controlled using control circuitry.

In some aspects, a flow rate of the drying expiratory limb is configured to improve breathability. For example, a cross-section of the drying expiratory limb can be increased to improve breathability.

In some aspects, the flow rate is decreased to improve breathability. In some aspects, a profile of an absolute humidity of the gas is substantially parallel to a profile of a dew point temperature of the gas. In some aspects, the drying expiratory limb is configured to substantially eliminate rain out at the first end of the tube and at the second end of the tube. In some aspects, the drying expiratory limb is configured to substantially eliminate rain out at a ventilator positioned at the second end of the tube.

Some embodiments provide for a drying expiratory limb for use in a respiratory circuit. The drying expiratory limb includes a wall having a first end and a second end separated by an expiratory limb length, the wall defining a space within and wherein at least a part of said wall comprises a breathable material configured to allow transmission of water vapor but substantially prevent transmission of liquid water. The drying expiratory limb includes a first opening in the first end of the wall, the first opening configured to receive a gas at a first temperature and a first relative humidity. The drying expiratory limb includes a second opening in the second end of the wall configured to allow the gas to exit the drying expiratory limb, the gas having a second temperature and a second relative humidity upon exiting the drying expiratory limb. The drying expiratory limb is configured such that the first relative humidity and the second relative humidity are approximately equal and a relative humidity of the gas at any point along the drying expiratory limb is approximately equal to the first relative humidity.

In some aspects, the relative humidity of the gas is at least about 95%, or at least about 99%. In some aspects, a decrease in temperature along the expiratory limb length is controlled according to a drying rate to keep the relative humidity at a targeted humidity value, where the targeted humidity value is between about 90% and about 99%, between about 95% and about 99%, or between about 95% and about 97%.

Some embodiments provide for a drying expiratory limb of a breathing circuit, the drying expiratory limb including a wall having a first end and a second end separated by an expiratory limb length, the wall defining a space within and wherein at least a part of said wall comprises a breathable material configured to allow transmission of water vapor but substantially prevent transmission of liquid water. The drying expiratory limb including a first opening in the first end of the wall, the first opening configured to receive a gas at a first temperature and a first relative humidity. The drying expiratory limb including a second opening in the second end of the wall configured to allow the gas to exit the drying expiratory limb, the gas having a second temperature and a second relative humidity upon exiting the drying expiratory limb. The drying expiratory limb is configured such that a temperature of the gas remains above a dew point temperature of the gas along the drying expiratory limb length. In some aspects, the drying expiratory limb is configured such that a difference in temperature of the gas and the dew point temperature of the gas along the drying expiratory limb length is approximately constant.

In some aspects, the drying expiratory limb also includes an insulating material on an outer surface of the wall. In a further aspect, the insulating material is configured to control the temperature of the gas to be between about 0.9° C. and 1° C. above the dew point temperature. In another aspect, an amount of the insulating material is substantially constant along the expiratory limb length. In another aspect, an amount of the insulating material varies along the expiratory limb length.

In some aspects, a rate of temperature decrease from the first end to a distance of about 300 mm from the first end is less than or equal to about 0.01° C./mm.

In some aspects, the drying expiratory limb further includes a heater wire configured to selectively receive electrical power to provide heat to the gas in the drying expiratory limb. In a further aspect, the heater wire is configured to control the temperature of the gas to be between about 0.9° C. and 1° C. above the dew point temperature. In another aspect, the drying expiratory limb further includes a second heater that is configured to control the rate of temperature decrease of the gas. In another aspect, the heater wire has a varying pitch spacing along the expiratory limb length. In a further aspect, the pitch spacing increases with distance from the first end. In another aspect, the heater wire comprises at least two sections, the two sections being configured to be independently controlled using control circuitry.

In some aspects, a flow rate of the drying expiratory limb is configured to improve breathability. In a further aspect, a cross-section of the drying expiratory limb is increased to improve breathability. In another aspect, the flow rate is decreased to improve breathability.

In some aspects, a profile of an absolute humidity of the gas is substantially parallel to a profile of the dew point temperature of the gas.

In some aspects, the drying expiratory limb is configured to substantially eliminate rain out at the first end of the wall and at the second end of the wall.

Some embodiments provide for a drying expiratory limb of a breathing circuit and the drying expiratory limb includes a wall having a first end and a second end separated by an expiratory limb length, the wall defining a space within and wherein at least a part of said wall comprises a breathable material configured to allow transmission of water vapor but substantially prevent transmission of liquid water. The drying expiratory limb includes a first opening in the first end of the wall, the first opening configured to receive a gas at a first temperature and a first relative humidity. The drying expiratory limb includes a second opening in the second end of the wall configured to allow the gas to exit the drying expiratory limb, the gas having a second temperature and a second relative humidity upon exiting the drying expiratory limb. The drying expiratory limb is configured such that the first relative humidity and the second relative humidity are approximately between about 90% and about 99%.

In some aspects, the first relative humidity of the gas or the second relative humidity of the gas or both are at least about 95%. In some aspects, the first relative humidity of the gas or the second relative humidity of the gas or both are at least about 99%. In some aspects, a decrease in temperature along the expiratory limb length is controlled according to a drying rate to keep a relative humidity of the gas along the expiratory limb length within a targeted relative humidity range. In a further aspect, the targeted relative humidity range is between about 90% and about 99%.

Some embodiments provide for a drying expiratory limb of a breathing circuit and the drying expiratory limb includes a wall having a first end and a second end separated by an expiratory limb length, the wall defining a space within and wherein at least a part of said wall comprises a breathable material configured to allow transmission of water vapor but substantially prevent transmission of liquid water. The drying expiratory limb includes a first opening in the first end of the wall, the first opening configured to receive a gas at a first temperature and a first relative humidity. The drying expiratory limb includes a second opening in the second end of the wall configured to allow the gas to exit the drying expiratory limb, the gas having a second temperature and a second relative humidity upon exiting the drying expiratory limb. The drying expiratory limb is configured such that a temperature of the gas remains approximately above a dew point temperature of the gas along the drying expiratory limb length, and a relative humidity of the gas remains approximately between about 90% and 99%.

In some aspects, the drying expiratory limb is configured such that the temperature of the gas remains approximately 1° C. above the dew point temperature of the gas along the drying expiratory limb length.

Some embodiments provide for a drying expiratory limb of a breathing circuit and the drying expiratory limb includes a wall having a first end and a second end separated by an expiratory limb length, the wall defining a space within and wherein at least a part of said wall comprises a breathable material configured to allow transmission of water vapor but substantially prevent transmission of liquid water. The drying expiratory limb includes a first opening in the first end of the wall, the first opening configured to receive a gas at a first temperature and a first relative humidity. The drying expiratory limb includes a second opening in the second end of the wall configured to allow the gas to exit the drying expiratory limb, the gas having a second temperature and a second relative humidity upon exiting the drying expiratory limb. The drying expiratory limb is configured such that a temperature of the gas remains approximately 1° C. above a dew point temperature of the gas along the drying expiratory limb length.

Some embodiments provide for a drying expiratory limb having a multi-lumen design for use in a respiratory circuit. The drying expiratory limb includes a multi-lumen configuration, each lumen having a first end and a second end and a space within the lumen defined by a wall, and at least a part of said wall comprises a breathable material configured to allow transmission of water vapor but substantially prevent transmission of liquid water. The drying expiratory limb includes a gas entry port configured to receive a gas at an entry temperature and an entry relative humidity for transmission along the drying expiratory limb. The drying expiratory limb includes a gas exit port configured to allow the gas to exit the drying expiratory limb, the gas having an exit temperature and an exit relative humidity upon exiting the drying expiratory limb. The drying expiratory limb is configured to increase a drying of the gas as it passes through the drying expiratory limb as compared to an expiratory limb comprising a single lumen of a similar size and a similar material. The drying expiratory limb is configured such that a difference between a temperature of the gas and a dew point temperature of the gas along the drying expiratory limb length is approximately constant.

In some aspects, the multi-lumen configuration comprises a plurality of tubes. In a further aspect, the plurality of tubes are configured to increase a surface area of the drying expiratory limb to increase drying along the drying expiratory limb and/or to decrease a flow rate in each lumen.

In some aspects, the drying expiratory limb further includes a heater wire configured to provide heat to the gas passing through the expiratory limb. In some aspects, the heater wire is configured to deliver a greater amount of heat to the gas near the entry port of the drying expiratory limb than to the gas near the exit port.

Some embodiments provide for a drying expiratory limb having a multi-lumen design for use in a respiratory circuit. The drying expiratory limb includes a multi-lumen configuration, each lumen having a first end and a second end and a space within the lumen defined by a wall, and at least a part of said wall comprises a breathable material configured to allow transmission of water vapor but substantially prevent transmission of liquid water. The drying expiratory limb includes a gas entry port configured to receive a gas at an entry temperature and an entry relative humidity for transmission along the drying expiratory limb. The drying expiratory limb includes a gas exit port configured to allow the gas to exit the drying expiratory limb, the gas having an exit temperature and an exit relative humidity upon exiting the drying expiratory limb. The drying expiratory limb is configured to increase a drying of the gas as it passes through the drying expiratory limb as compared to an expiratory limb comprising a single lumen of a similar size and a similar material. The drying expiratory limb is configured such that the first relative humidity and the second relative humidity are approximately equal and a relative humidity of the gas at any point along the drying expiratory limb is approximately equal to the first relative humidity.

Some embodiments provide for a drying expiratory limb of a breathing circuit and the drying expiratory limb includes a multi-lumen configuration, wherein each lumen has a first end and a second end and a space within the lumen defined by a wall, at least a part of said wall comprises a breathable material configured to allow transmission of water vapor but substantially prevent transmission of liquid water. The drying expiratory limb includes a gas entry port configured to receive a gas at an entry temperature and an entry relative humidity for transmission along the expiratory limb. The drying expiratory limb includes a gas exit port configured to allow the gas to exit the expiratory limb, the gas having an exit temperature and an exit relative humidity upon exiting the expiratory limb. The multi-lumen design is configured to increase a drying of the gas as it passes through the expiratory limb as compared to an expiratory limb comprising a single lumen of a similar size and a similar material. The drying expiratory limb is configured such that a temperature of the gas remains above a dew point temperature of the gas along the drying expiratory limb length.

In some aspects, the multi-lumen configuration comprises a plurality of tubes. In a further aspect, the plurality of tubes is configured to increase a surface area of the expiratory limb to increase drying along the expiratory limb. In another aspect, the plurality of tubes is configured to decrease a flow rate in each lumen.

In some aspects, the drying expiratory limb further includes a heater wire configured to provide heat to the gas passing through the expiratory limb. In a further aspect, the heater wire is configured to deliver a greater amount of heat to the gas near the entry port of the expiratory limb than to the gas near the exit port.

In some aspects, the number of lumens is less than or equal to 5.

Some embodiments provide for a drying expiratory limb of a breathing circuit and the drying expiratory limb includes a multi-lumen configuration, wherein each lumen has a first end and a second end and a space within the lumen defined by a wall, at least a part of said wall comprises a breathable material configured to allow transmission of water vapor but substantially prevent transmission of liquid water. The drying expiratory limb includes a gas entry port configured to receive a gas at an entry temperature and an entry relative humidity for transmission along the expiratory limb. The drying expiratory limb includes a gas exit port configured to allow the gas to exit the expiratory limb, the gas having an exit temperature and an exit relative humidity upon exiting the expiratory limb. The multi-lumen design is configured to increase a drying of the gas as it passes through the expiratory limb as compared to an expiratory limb comprising a single lumen of a similar size and a similar material. The drying expiratory limb is configured such that the first relative humidity and the second relative humidity are approximately between about 90% and about 99%. In some aspects, the number of lumens is less than or equal to 5.

Some embodiments provide for a drying expiratory limb for use in a respiratory circuit and the drying expiratory limb includes a multi-lumen configuration comprising less than six lumens, wherein each lumen has a first end and a second end and a space within the lumen defined by a wall, at least a part of said wall comprises a breathable material configured to allow transmission of water vapor but substantially prevent transmission of liquid water. The drying expiratory limb includes a gas entry port configured to receive a gas at an entry temperature and an entry relative humidity for transmission along the expiratory limb. The drying expiratory limb includes a gas exit port configured to allow the gas to exit the expiratory limb, the gas having an exit temperature and an exit relative humidity upon exiting the expiratory limb. The multi-lumen design is configured to increase a drying of the gas as it passes through the expiratory limb as compared to an expiratory limb comprising a single lumen of a similar size and a similar material.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIG. 3 illustrates a drying expiratory limb with varying insulation to control the temperature of the gas along the tube.

FIG. 4 illustrates a drying expiratory limb with two sections that include breathable insulation to control a temperature drop at a beginning of the tube and at an end of the tube.

FIG. 5 illustrates a drying expiratory limb having multiple heater wires that have a pitch spacing that is different in different sections.

FIG. 6 illustrates a drying expiratory limb having a coiled heater wire that has a pitch spacing that is different in different sections.

FIG. 7 illustrates a drying expiratory limb having a straight heater wire with zones of varying pitch spacing within the wire.

FIG. 8 illustrates a drying expiratory limb having multiple sections wherein a system is configured to independently control the different sections of heater wire.

FIG. 9 illustrates a drying expiratory limb having a heater wire that is folded back upon itself at a patient end to control a temperature drop at a front end of the drying expiratory limb.

FIG. 10 illustrates a drying expiratory limb combining a varying insulation layer with a heater wire with a varying pitch.

FIGS. 11A-19B illustrate various multi-lumen configurations for a drying expiratory limb.

FIGS. 20A-25B illustrate drying expiratory limbs configured to increase a surface area using different cross-section shapes.

FIG. 15 FIGS. 29-33 illustrates various multi-lumen configurations for a drying expiratory limb.

DETAILED DESCRIPTION

Figure 1:
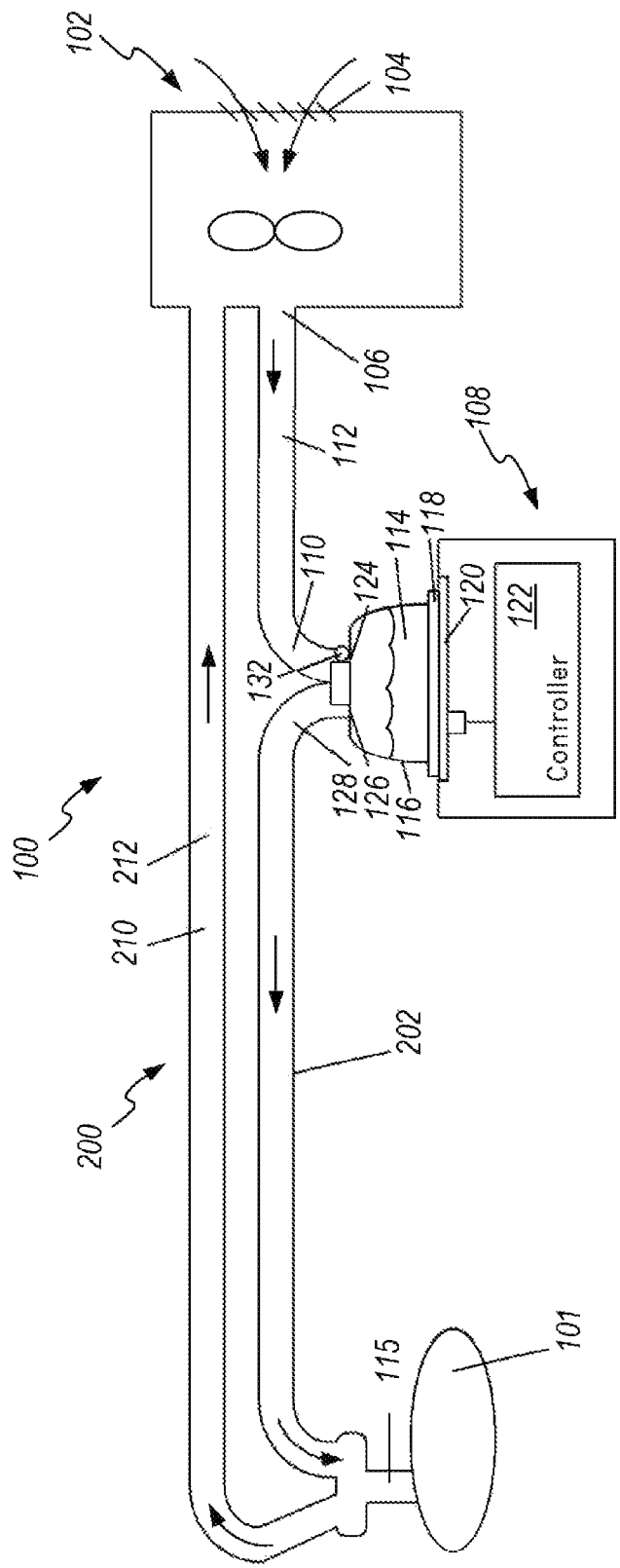
FIG. 1 illustrates an example respiratory system for delivering humidified gas to a user, the respiratory humidification system having a breathing circuit that includes a drying expiratory limb configured to have a linear temperature profile as a function of distance along the drying expiratory limb.

Certain embodiments and examples of expiratory limbs are described herein. Those of skill in the art will appreciate that the disclosure extends beyond the specifically disclosed embodiments and/or uses and obvious modifications and equivalents thereof. Thus, it is intended that the scope of the disclosure not be limited by any particular embodiments described herein.

Descriptions of expiratory limbs are presented herein that include breathable material configured to pass water vapor and to substantially prevent liquid water from passing through. Any suitable breathable material can be used. As an example, sample breathable materials are described in Applicant's PCT Publication WO 2011/077250, entitled "Components for Medical Circuits," filed Dec. 22, 2010, which is hereby incorporated by reference in its entirety and made a part of this specification. For example, the breathable material can be a breathable foamed material configured to allow the transmission of water vapor but substantially prevent the transmission of liquid water. The breathable foamed material can comprise a blend of polymers. The breathable foamed material can comprise a thermoplastic elastomer with a polyether soft segment. The breathable foamed material can comprise a copolyester thermoplastic elastomer with a polyether soft segment. The breathable foamed material can comprise a thermoplastic elastomer with a polyether soft segment.

Expiratory limbs can be included in medical circuits such as breathing circuits for use in respiratory applications. It is desirable, as described herein, to provide a drying expiratory limb in a respiratory circuit that is breathable. Breathability is desirable to reduce or prevent rain out. Furthermore, it may be advantageous to control the temperature and/or relative humidity of the gas passing through the drying expiratory limb to limit or prevent condensation in a ventilator, rain out in the tube, to increase drying of the gas, or any combination of these. Passive and active solutions for controlling the temperature of the gas passing through a drying expiratory limb are presented herein.

For an unheated expiratory limb, as the gas travels along the tube towards a ventilator, ambient, or gas source, the gas will cool at a rate that is higher than its drying rate. As a result, the temperature of the gas can drop below the dew point temperature, causing condensation to form inside the expiratory limb. For a heated expiratory limb, the gas may be kept at a high temperature for too long. As the gas dries, the relative humidity of the gas can drop (as the temperature of the gas is relatively constant over a portion of the tube), which impairs further drying, as drying is more efficient when the relative humidity is at or near about 100%. If the gas has not been dried enough, when the temperature drops in the ventilator then condensation can form in the ventilator.

Accordingly, it may be advantageous to improve or optimize drying along the length of the drying expiratory limb, which can be accomplished, in some embodiments, by maintaining the relative humidity at a substantially constant value. In some embodiments, improved or optimized drying may occur where the relative humidity remains between about 90% and about 99%, between about 95% and about 99%, or between about 95% and about 97%. It may also be advantageous to reduce the temperature of the gas along the length of the tube so that the temperature of the gas exiting the drying expiratory limb is at or near the temperature of the ventilator, gas source, or ambient. An effective method of doing this is to have the humidity and/or temperature decrease in a tailored manner along the length of the tube. For example, it may be advantageous to tailor the rate of temperature decrease across the first portion of the drying expiratory limb so that it does not exceed about $-0.01°$ C./mm, or so that the temperature drop is between about $0°$ C./mm and about $-0.009°$ C./mm. In some embodiments, it may be advantageous to limit the rate of temperature decrease to the stated ranges from the beginning of the tube to about the first 300 mm or 400 mm of the drying expiratory limb. It may be advantageous to also limit the total temperature drop across the tube to be less than or equal to about $10°$ C. and/or between about $3°$ C. and $10°$ C. In some embodiments, drying within a tube is limited by the relative humidity. In some embodiments, it may be desirable to have the temperature drop in a linear or a nearly linear fashion along the tube. Therefore, the drying expiratory limbs described herein have been configured to achieve the goals of reducing or eliminating rain out or condensation in the ventilator through controlling the environment within the tube. For example, for a gas with a relative humidity of about 95%, the drying expiratory limb can be configured to tailor the temperature profile such that the difference between the temperature of the gas and the dew point temperature is less than about $1.5°$ C., less than about $1°$ C., or between about $0.9°$ C. and about $1°$ C. The heating or insulation of the tube can be configured to keep the temperature within a "non-condensation window" which can be a temperature range that lies between the dew point temperature line and the absolute humidity line so that little or no condensation occurs within the drying expiratory limb or at the ventilator.

In some embodiments, an example temperature profile that reduces condensation, reduces rain out, and that provides the advantageous properties described herein can be where an initial temperature drop (e.g., from the patient interface) from the beginning of the tube to about the first 300 or 400 mm can have a slope that is between about $0°$ C./mm and about $-0.01°$ C./mm. In some embodiments, a temperature profile that has a total drop in temperature between about $3°$ C. and about $10°$ C. may provide at least some of the advantages set forth herein.

Embodiments of drying expiratory limbs will be now described herein with reference to their use in a respiratory system. It is to be understood, however, that the drying expiratory limbs described herein can be used with incubation systems, surgical humidification systems, and the like where it may be desirable to avoid condensation in the tube when delivering gas from a first environment to a second environment, the two environments having different temperatures and/or humidity.

FIG. 1 illustrates an example respiratory system 100 for delivering humidified gas to a user, the humidification system 100 having a breathing circuit 200 that includes an inspiratory limb 202 and an expiratory limb 210. The illustrated respiratory humidification system 100 comprises a pressurized gas source 102. In some implementations, the pressurized gas source 102 comprises a fan, blower, or the like. In some implementations, the pressurized gas source 102 comprises a ventilator or other positive pressure generating device. The pressurized gas source 102 comprises an inlet 104 and an outlet 106.

The pressurized gas source 102 provides a flow of fluid (e.g., oxygen, anesthetic gases, air or the like) to a humidification unit 108. The fluid flow passes from the outlet 106 of the pressurized gas source 102 to an inlet 110 of the humidification unit 108. In the illustrated configuration, the humidification unit 108 is shown separate of the pressurized gas source 102 with the inlet 110 of the humidification unit 108 connected to the outlet 106 of the pressurized gas source 102 with a conduit 112. In some implementations, the pressurized gas source 102 and the humidification unit 108 can be integrated into a single housing.

The gases flow through the inspiratory limb 202 to the patient 101 through a patient interface 115. The expiratory limb 210 also connects to the patient interface 115. The expiratory limb 210 is configured to move exhaled humidified gases away from the patient 101. Here, the expiratory limb 210 returns exhaled humidified gases from the patient interface 115 to the gases source 102. Alternatively, exhaled humidified gases can be passed directly to ambient surroundings or to other ancillary equipment, such as an air scrubber/filter (not shown). Any suitable patient interface 115 can be incorporated. Patient interface is a broad term and is to be given its ordinary and customary meaning to a person of ordinary skill in the art (that is, it is not to be limited to a special or customized meaning) and includes, without limitation, masks (such as face masks and nasal masks), cannulas, and nasal pillows. A patient interface usually defines a gases space which, when in use, receives warm humid breathing gases.

While other types of humidification units can be used with certain features, aspects, and advantages described in the present disclosure, the illustrated humidification unit 108 is a pass-over humidifier that comprises a humidification chamber 114 and an inlet 110 to the humidification chamber 114. In some implementations, the humidification chamber 114 comprises a body 116 having a base 118 attached thereto. A compartment can be defined within the humidification chamber 116 that is adapted to hold a volume of liquid that can be heated by heat conducted or provided through the base 118. In some implementations, the base 118 is adapted to contact a heater plate 120. The heater plate 120 can be controlled through a controller 122 or other suitable component such that the heat transferred into the liquid can be varied.

The controller 122 of the humidification unit 108 can control operation of various components of the respiratory humidification system 100. While the system as illustrated uses a single controller 122, multiple controllers can be used in other configurations. The multiple controllers can communicate or can provide separate functions and, therefore, the controllers need not communicate. In some implementations, the controller 122 may comprise a microprocessor, a processor, or logic circuitry with associated memory or storage that contains software code for a computer program. In such implementations, the controller 122 can control operation of the respiratory humidification system 100 in accordance with instructions, such as contained within the computer program, and also in response to internal or external inputs.

The body 116 of the humidification chamber 114 comprises a port 124 that defines the inlet 110, and a port 126 that defines an outlet 128 of the humidification chamber 114. As liquid contained within the humidification chamber 114 is heated, liquid vapor is mixed with gases introduced into the humidification chamber 114 through the inlet port 124. The mixture of gases and vapor exits the humidification chamber 114 through the outlet port 126.

The humidification system 100 includes a breathing circuit 200 comprising the inspiratory limb 202 connected to the outlet 128 that defines the outlet port 126 of the humidification unit 108. The inspiratory limb 202 conveys toward a user the mixture of gases and water vapor that exits the humidification chamber 114. The inspiratory limb 202 can include a heating element 206 positioned along the inspiratory limb 202, wherein the heating element 206 is configured to reduce condensation along the inspiratory limb 202, to control a temperature of gas arriving at the user, or both. The heating element 206 can raise or maintain the temperature of the gases and water vapor mixture being conveyed by the inspiratory limb 202. In some implementations, the heating element 206 can be a wire that defines a resistance heater. By increasing or maintaining the temperature of the gases and water vapor mixture leaving the humidification chamber 114, the water vapor is less likely to condensate out of the mixture.

The humidification system 100 includes an expiratory limb 210 configured to carry away expired gas from the user and deliver it to the gas source 102. The expiratory limb 210 can include a wall having a first end at the patient end to receive the expired or exhaled gas and a second end at the gas source 102, the two ends being separated by an expiratory limb length. The wall can define a space for the gas to travel (e.g., one or more lumens) and at least a portion of the wall can include a breathable material.

If the gas cools too quickly along the expiratory limb 210, the gas can become supersaturated as the water vapor cannot pass through the breathable layer quickly enough. This can cause, at least in part, rain out near the patient end of the expiratory limb 210. If the gas cools too slowly, rain out can form near the second end of the expiratory limb 210, where the relatively hot gas comes into contact with cooler air at the gas source 102 or ambient. To reduce or prevent rain out in the expiratory limb, characteristics of the gas or the expiratory limb 210 can be controlled. For example, by controlling the temperature profile of the gas and other variables in the expiratory limb 210, the breathability of the expiratory limb 210 can be improved. In some embodiments, the breathability of the expiratory limb 210 can increase by increasing transit time through the expiratory limb 210, which can be accomplished, in some embodiments, by decreasing a flow rate or by increasing a length of the passage through expiratory limb 210. Increasing the transit time through the expiratory limb may, in some implementations, increase heat loss of the gas through the expiratory wall. If this occurs too quickly, as stated above, rain out can occur. In some embodiments, providing a substantially linear temperature profile along the expiratory limb 210 and/or increasing a transit time through the expiratory limb 210 can increase the breathability of the expiratory wall by about 40% to about 70% or more. Accordingly, in some embodiments, the expiratory limb 210 can be configured to have a substantially linear temperature profile such that the temperature of the gas drops in a linear fashion across the length of the expiratory limb 210. Relatedly, in some embodiments, the expiratory limb 210 can be configured to keep a difference between the gas temperature and its dew point temperature substantially constant across the length of the expiratory limb 210. Similarly, in some embodiments, the expiratory limb 210 can be configured to keep a relative humidity of the gas at between about 95% to about 99% across the length of the expiratory limb 210.

In some embodiments, the expiratory limb 210 includes insulation configured to control a temperature profile in the expiratory limb. In some embodiments, the expiratory limb 210 includes an associated heating element 212 that is arranged along the expiratory limb 210, wherein the heating element 212 is configured to maintain a substantially linear temperature drop along the expiratory limb 202, to control a relative humidity of the gas, to control a temperature of the gas relative to its dew point temperature, or any combination of these.

The heating element 212 can be selectively controlled by the controller 122 in the humidification system 100 or through other means. The controller 122 can be configured to control the heating element 210, to receive feedback from sensors in the system, to provide logic to control power to the heating element 212, to adjust control of the heating element 212 in response to temperature readings from sensors, and the like. In some embodiments, the controller 122 includes a power source configured to deliver electrical power to the heating element 212. The controller 122, for example, can control an amount of heat delivered by the heating element 212 by delivering a variable power, a variable current, a variable voltage, or any combination of these to the heating element 212. The controller 122 can implement pulse-width-modulation to control the heating element 212. The controller 122 can apply a substantially constant electrical power until a desired temperature is reached within the expiratory limb 210. In some embodiments, the expiratory limb 210 includes one or more sensors configured to provide the controller or a user with information regarding the characteristics of the gas in the expiratory limb 210 which can include, for example, temperature, relative humidity, absolute humidity, or any combination of these and this information can be provided at one or more points along the expiratory limb 210. In some implementations, the heating element 206 can be a wire that defines a resistance heater.

In some embodiments, the expiratory limb 210 can include insulation in combination with the heating element 212. In some embodiments, the heating element 210 can be configured to provide zone heating capabilities such that different portions of the expiratory limb 210 receive different amounts of heat. This can be accomplished, for example, by using multiple heating wires or a single wire with different winding densities or pitch spacing at different points.

In some embodiments, the drying expiratory limb 210 can comprise multiple tubes, which can increase an effective ratio of the surface area of the drying expiratory limb 210 to its cross-section. The multi-tube construction can be self-reinforcing, which can reduce a need for reinforcing structures like ribs, which can result in a thinner wall. The multi-tube construction can comprise multiple tubes spiraled or braided together. This may be advantageous because each tube ends up being longer than the expiratory limb length, increasing the transit time through the drying expiratory limb 210. This can be in addition to the increase in surface area, which may also be advantageous.

Example Expiratory Limbs with Tailored Temperature Profiles

Figure 2:
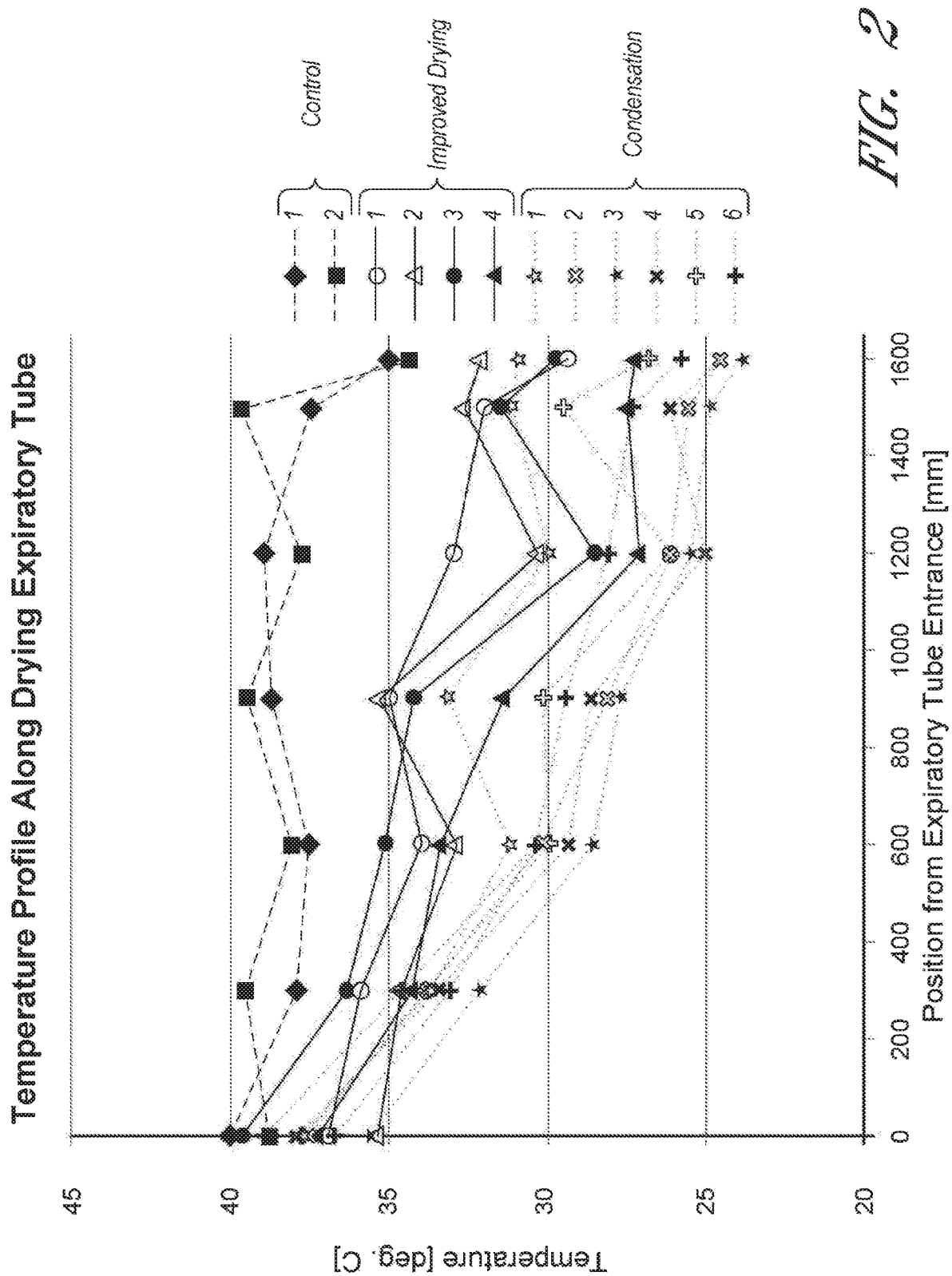
FIG. 2 illustrates a plot of a temperature of a gas as a function of position along an expiratory limb.

FIG. 2 illustrates a plot of a temperature of a gas as a function of position along an expiratory limb. The two plots listed as "Control" and shown with dashed lines illustrate some expiratory limbs that have been configured to dry gases using breathable materials. The four plots listed as "Improved Drying" and shown with solid lines illustrate results when using some embodiments described herein. They represent an improved or optimized drying of the gases through the drying expiratory limbs. The six plots listed as "Condensation" and shown with dotted lines represent expiratory limbs with temperature profiles that experience rain out or condensation within the tube or at the ventilator. These expiratory limbs experience a rate of temperature decrease from the beginning of the expiratory limb to about 300 mm or 400 mm that exceeds about −0.009° C./mm or about −0.01° C./mm and/or where the total temperature drop exceeds about 10° C. or is between about 3° C. and about 10° C.

Table 1 lists information related to the absolute humidity and dew point temperature for the temperature profiles of the two "Control" plots and the 4 "Improved Drying" plots in FIG. 2. The table lists the input absolute humidity ("AH In") and the output absolute humidity ("AH Out") and the dew point temperature ("DPT") of the exit gas.

TABLE 1

Absolute humidity and dew point temperature of example drying expiratory tubes

| Sample | AH In [mg/L] | AH Out [mg/L] | DPT [deg C.] |
| --- | --- | --- | --- |
| Control 1 | 44.1 | 35.0 | 32.7 |
| Control 2 | 43.4 | 28.3 | 28.7 |
| Improved 1 | 43.4 | 25.1 | 26.5 |
| Improved 2 | 45.3 | 26.5 | 27.5 |
| Improved 3 | 42.3 | 26.3 | 27.4 |
| Improved 4 | 43.2 | 24.9 | 26.4 |

Example Drying Expiratory Limbs

Example configurations of drying expiratory limbs will now be described. The various embodiments described herein and illustrated in the figures are intended to be illustrative of various implementations that achieve a stated goal of reducing condensation in a ventilator and/or rain out in the drying expiratory limb. Many different variations and permutations are possible which do not depart from the scope of the examples provided herein. Thus, it is to be understood that the following examples should not be interpreted as limiting the scope of the disclosure, and the scope of the present disclosure extends beyond these enumerated examples.

Generally, the example drying expiratory limb designs can be configured to address situations where radiation of energy from the expiratory limb to ambient or the external atmosphere can cause too rapid a temperature drop at the entrance to the expiratory limb, which can cause condensation in this section of the tube. This situation can be common when the external temperature is relatively low, flow rate is relatively low and/or external relative humidity is relatively high (factors which can reduce breathability of the expiratory limb). Under such conditions it may be advantageous to decrease the rate of temperature change.

Relatedly, if conditions are present that limit or reduce the breathability of the expiratory limb, then it may be advantageous to have a relatively high exit temperature to limit condensation at the exit of the tube (e.g., upon entering the ventilator or gas source). For example, where the external relative humidity is relatively high or when the flow rate is relatively high, the breathability of the expiratory limb may be reduced.

Thus, example drying expiratory limbs are included and described herein that can be configured to deal with a wide range of conditions that may cause condensation. These designs could be modified where it is more desirable to address one condition over another or to enhance or improve efficacy related to a particular problem. The drying expiratory limbs presented herein can be configured to address situations where external temperature is relatively low, flow rate is relatively low, or external relative humidity is relatively high.

FIG. 3 illustrates a drying expiratory limb 210 with varying insulation 214 to control the temperature of the gas along the tube. The single conduit has several different sections having different insulation values. The insulation values are represented in FIG. 3 as different sizes of insulating material 214. However, the physical sizes of the insulating elements 214 do not have to decrease along the length and the sizes can be substantially identical along the length. To increase the effect of insulating elements 214, a thickness of the insulating material 214 can be increased, a density of the insulating material 214 can be increased, different materials can be used, etc. The insulating values can be configured to provide a relatively linear or slightly concave temperature profile over a range of temperature conditions, relative humidity, and/or flow rates. In some embodiments, the insulation sections along the tube are not discrete, but can be substantially continuous, or it can be configured to have insulation sections that change in a substantially continuous manner combined with sections that provide a discrete change in insulation value. The number of insulating sections can be any suitable number including, for example, 2, 3, 4, 5, 6, 7, 8, 10, 15, 20, 50, or more.

FIG. 4 illustrates a drying expiratory limb 210 with two sections that include breathable insulation 214 to control a temperature drop at a beginning of the tube and at an end of the tube. This configuration may be advantageous because the insulation material 214 is used where gas tends to experience relatively rapid cooling. The insulation values, extent of insulation, and placement of the insulation 214 can be configured to provide the advantages described herein. Additional insulating sections may be included as well.

FIG. 5 illustrates a drying expiratory limb 210 having multiple heater wires 212 that have a pitch spacing that is different in different sections or a single heater wire 212 with varying pitch spacing or a combination of both. This represents an active temperature control mechanism. As such, the heater wire or wires 212 can be coupled to the controller 122, as described herein with reference to FIG. 1, with the attendant control mechanisms described there. Similarly, the heater wires illustrated in FIGS. 4-9 can be controlled using the heater wire.

The heater wires 212 can be configured to be outside the tubing and can have different spacing along the tube. Near the patient end, the spacing can be relatively close together to generate or apply more heat compared to the heat applied closer to the tube exit. In some embodiments, there can be different zones with different winding densities to achieve a near linear temperature profile. In some embodiments, the number of sections with different spacing can be 2, 3, 4, 5, 6, 7, 8, 10, 15, 20, 25, 50, or more or the spacing of the windings can increase substantially smoothly with distance from the patient end. In some embodiments, the heater wire 212 comprises multiple, individual heating elements which can be collectively and/or individually controlled.

FIG. 6 illustrates a drying expiratory limb 210 having a coiled heater wire 212 that has a pitch spacing that is different in different sections. The heater wire 212 can be positioned within the tube. The winding configuration can be similar to the configurations described herein with reference to FIG. 5. In some embodiments, the heater wire 212 comprises multiple, individual heating elements which can be collectively and/or individually controlled.

FIG. 7 illustrates a drying expiratory limb 210 having a straight heater wire with zones of varying pitch spacing within the wire. The pitch spacing can be configured similar to the winding density and spacing described herein with reference to FIGS. 5 and 6. In some embodiments, the heater wire 212 comprises multiple, individual heating elements which can be collectively and/or individually controlled.

FIG. 8 illustrates a drying expiratory limb 210 having multiple heater sections wherein a system is configured to independently control the different sections of heater wire 212. As shown, the heater is divided into sections which can be selectively controlled by the controller 122 through the connectors 216a and 216b. There can be more sections with accompanying connectors, and the description here is limited to three sections with two connectors.

Connectors 216a and 216b couple the first and second heater segments and allow the controller to selectively apply heat to different sections of the drying expiratory limb 210. The connectors 216a, 216b can be configured to electrically couple the heater wires 212 in the segments to enable control of the heater wires 212 using the controller 122. The connector 216a, 216b can be configured to electrically couple temperature sensors (not shown) to enable the controller 122 to acquire their respective outputs. The connectors 216a, 216b can include electrical components that enable selective control of the heater wires 212. For example, the connectors 216a, 216b can include electrical components that direct power through the heater wires 212 in a first section in a first operation mode and through the heater wires 212 in both the first section and a second section in a second operation mode. The electrical components included on the connector 216a, 216b can include, for example and without limitation, resistors, diodes, transistors, relays, rectifiers, switches, capacitors, inductors, integrated circuits, micro-controllers, micro-processors, and the like. In some embodiments, the connector 216a, 216b can be configured to be internal to the drying expiratory limb 210 such that it is substantially shielded from external elements. In some embodiments, some of the electrical components on the connector 216a, 216b can be configured to be physically isolated from the humidified gas within the drying expiratory limb 210 to reduce or prevent damage that may result from exposure to humidity. In some embodiments, the connector 216a, 216b can include relatively inexpensive passive electrical components to reduce cost and/or increase reliability.

FIG. 9 illustrates a drying expiratory limb 210 having a heater wire 212 that is folded back upon itself at a patient end to control a temperature drop at a front end of the drying expiratory limb 210. The extent of the folding can be configured to provide a desired or advantageous temperature profile near the patient end of the limb 210. For example, it may be advantageous to limit the initial temperature drop to reduce condensation at the patient inlet so providing additional heat at this location may reduce or prevent rain out near the inlet.

FIG. 10 illustrates a drying expiratory limb 210 combining a varying insulation layer 214 with a heater wire 212 with a varying pitch. This embodiment is similar to combining the elements from FIG. 3 and FIG. 6. The sections of relatively constant insulation value and relatively constant winding density need not coincide. Transitions between insulation values and/or winding densities can be varied and can be independent from one another. This embodiment also illustrates that passive and active control approaches may be utilized in the drying expiratory limb 210.

FIGS. 11 through 15 illustrate some embodiments of drying expiratory limbs employing a multi-lumen design. This can advantageously provide for a relatively larger surface area to cross-section ratio for a drying expiratory limb which can increase breathability. In some embodiments, the drying expiratory limb comprises multiple single tubes twisted or braided together. This may advantageously provide for an increased time in the tube for the gas because the length of the individual tubes is longer due at least in part to the twisting, while the overall length of the bundle is kept to an acceptable length. The longer single tube length can improve breathability, for example. In some embodiments, increasing void fractions or spaces between tubes can improve insulation.

FIGS. 11A-19B illustrate various multi-lumen configurations of drying expiratory limbs 210. The multi-lumen limb 210 can include two or more individual tubes 211 joined together in various ways and in various geometrical configurations. In some embodiments, the tubes are physically separated from one another to allow an increase in breathability through the tube wall. In some embodiments, the drying expiratory limb 210 can include insulation material 214 surrounding the bundled tubes 211, as illustrated in FIGS. 16A-19B. Several geometrical configurations are illustrated in FIGS. 11A-19B, but other configurations are possible as well. For example, FIGS. 20A-25B illustrate drying expiratory limbs 210 that do not comprise multiple individual tubes but which are configured to increase a ratio of the surface area to cross-section using different cross-section shapes. FIGS. 24A-25B, in particular, illustrates that many different cross-section shapes are possible including regular or irregular shapes. In addition, any of the foregoing multi-lumen embodiments may include insulation material 214, as illustrated in FIGS. 24A-25B. In some embodiments, the shape of the tube or tubes 211 can change along the length of the drying expiratory limb. For example, the tube 211 can have a generally circular shape near the patient end of the tube which can change to a triangle somewhere along the length, which can then change to a star shape or shape similar to any of the embodiments in FIG. 11C or 11D FIGS. 20A-25B. This can change the ratio of the surface area to the cross section over the length of the tube, affecting the breathability and, hence, the temperature profile.

Figure 26:
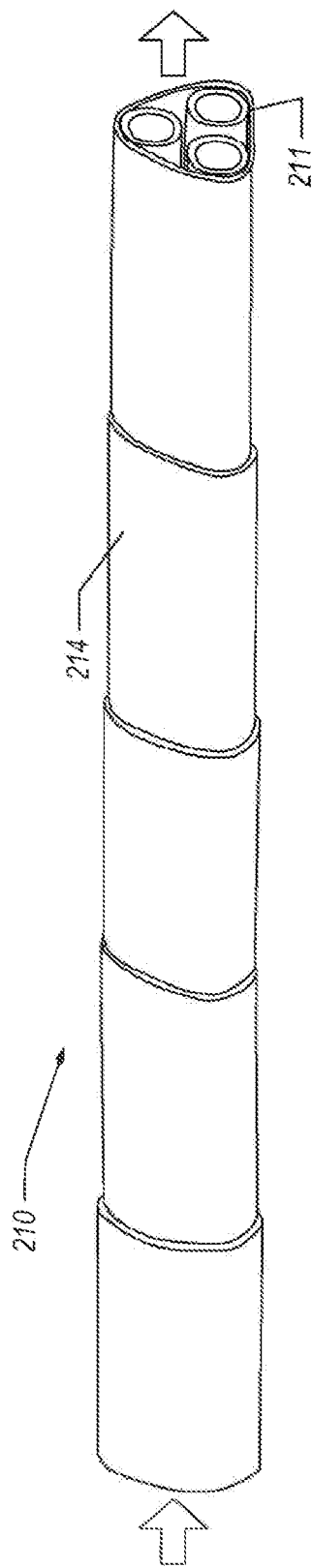
FIG. 26 illustrates a drying expiratory limb combining multiple tubes and varying insulation.

FIG. 26 illustrates a drying expiratory limb 210 combining multiple tubes 211 and varying insulation 214. This drying expiratory limb 210 represents a passive temperature control approach to the multi-lumen design. In some embodiments, using the multi-lumen design can increase the breathability of the drying expiratory limb 210. Using the insulation material 214 can decrease a rate of cooling that may increase where breathability increases. The insulation material can be configured to reduce cooling while not adversely affecting the breathability of the expiratory limb 210.

Figure 27:
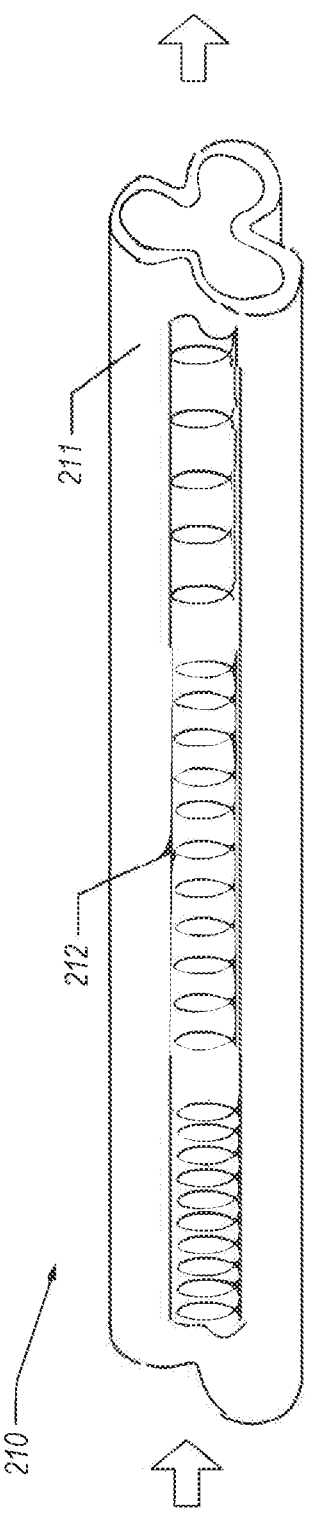
FIG. 27 illustrates a drying expiratory limb with a cross-section similar to the drying expiratory limbs illustrated in FIGS. 24A-25B and a heater wire with a varying pitch spacing along its length.
Figure 28:
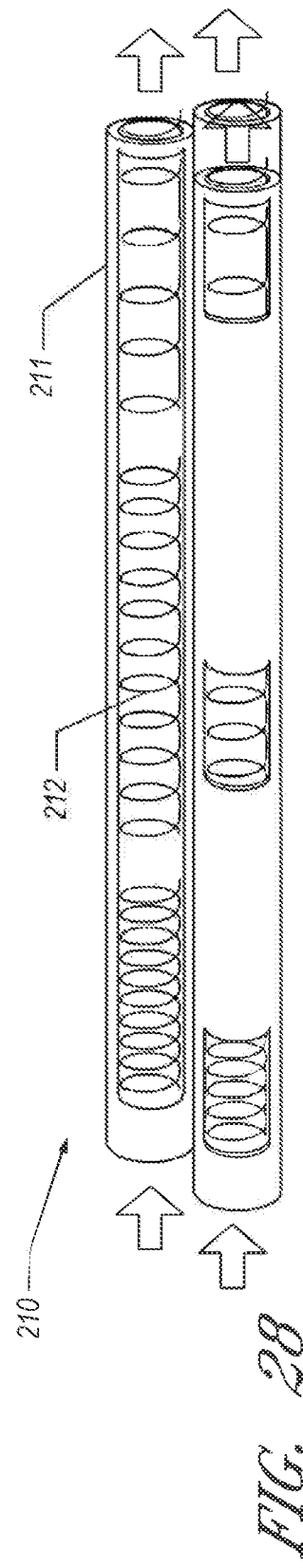
FIG. 28 illustrates a drying expiratory limb with a multi-lumen design in conjunction with heater wires in each lumen.
Figure 29:
Figure 30:
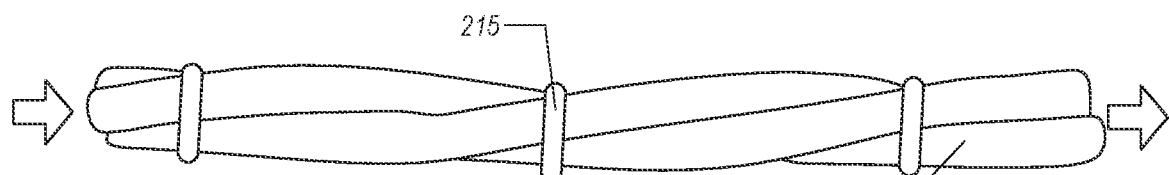
Figure 31:
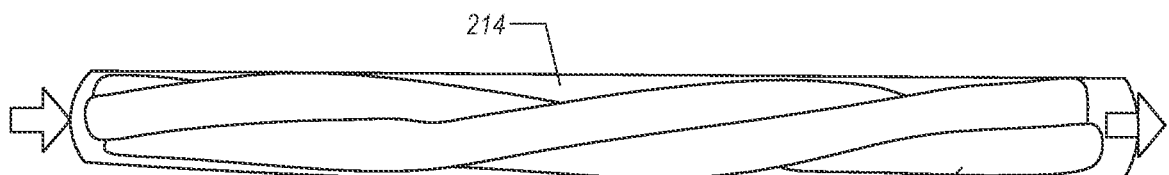
Figure 32:
Figure 33:
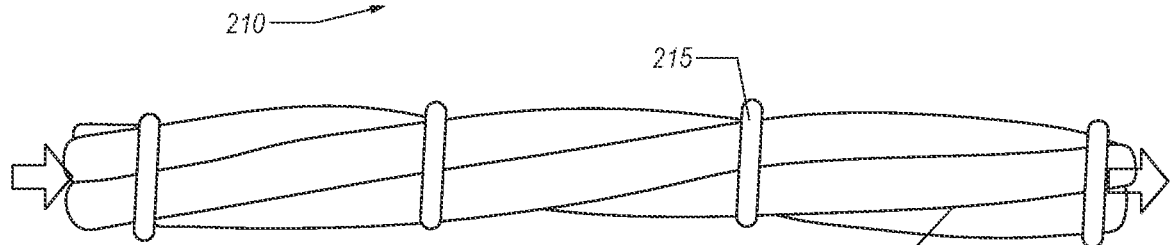

The drying expiratory limbs 210 illustrated in FIGS. 13 and 14 illustrate active approaches to temperature control in conjunction with the multi-lumen designs of FIG. 11A-25B. FIG. 27 illustrates a drying expiratory limb 210 with a cross-section similar to the drying expiratory limbs 210 illustrated in FIG. FIGS. 24A-25B and a heater wire 212 with a varying pitch spacing along its length, similar to the drying expiratory limbs described with reference to FIGS. 6 and 10. In some embodiments, using the multi-lumen design can increase the breathability of the expiratory limb 210. Heater wires 212 can be used to limit the cooling of the gas that may arise due to the increase in breathability with the multi-lumen drying expiratory limbs 210. FIG. 28 illustrates a drying expiratory limb 210 with a multi-lumen design in conjunction with heater wires 212 in each individual tube 211.

FIGS. 29-33 illustrates various multi-lumen configurations for a drying expiratory limb 210. The individual tubes 211 can be twisted around each other for mechanical stability and/or support. By twisting the individual tubes, each tube's length is greater than the length of the resulting drying expiratory limb 210. This can increase the time the gas spends in the drying expiratory limb which can result in a more advantageous temperature profile, breathability, and reduction in rain out. In some embodiments, the multiple individual tubes 211 can be held together using adhesives. In some embodiments, the multiple individual tubes can be held together using securing mechanisms 215 such as clips, rubber bands, ties, or the like. In some embodiments, the individual tubes can be held together using a sheath 214, where the sheath 214 can also be insulative and/or the sheath 214 can be configured to be aesthetically pleasing. The number of twisted tubes can be, for example, 2, 3, 4, 5, or more than 5.

CONCLUSION

Examples of drying expiratory limbs having linear temperature profiles and/or substantially constant relative humidity profiles along the length of the tube have been described with reference to the figures. The representations in the figures have been presented to clearly illustrate principles related to drying expiratory limbs with linear temperature profiles, and details regarding divisions of modules or systems have been provided for ease of description rather than attempting to delineate separate physical embodiments. The examples and figures are intended to illustrate and not to limit the scope of the embodiments described herein. For example, the principles herein may be applied to tubes for use in other circuits as well as respiratory circuits, including surgical humidifiers. The principles herein may be applied in respiratory applications as well as in other scenarios where a temperature of gases along a length of a tube is desired to be approximately linear.

As used herein, the term "processor" refers broadly to any suitable device, logical block, module, circuit, or combination of elements for executing instructions. For example, the controller 122 can include any conventional general purpose single- or multi-chip microprocessor such as a Pentium® processor, a MIPS® processor, a Power PC® processor, AMD® processor, ARM® processor, or an ALPHA® processor. In addition, the controller 122 can include any conventional special purpose microprocessor such as a digital signal processor. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. Controller 122 can be implemented as a combination of computing devices, e.g., a combination of a DSP and a microprocessor, a plurality of microprocessors, one or more microprocessors in conjunction with a DSP core, or any other such configuration.

Data storage can refer to electronic circuitry that allows information, typically computer or digital data, to be stored and retrieved. Data storage can refer to external devices or systems, for example, disk drives or solid state drives. Data storage can also refer to fast semiconductor storage (chips), for example, Random Access Memory (RAM) or various forms of Read Only Memory (ROM), which are directly connected to the communication bus or the controller 122. Other types of memory include bubble memory and core memory. Data storage can be physical hardware configured to store information in a non-transitory medium.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments. As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z each to be present.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

What is claimed is:

1. A breathing circuit comprising:
   an inspiratory limb; and
   a drying expiratory limb comprising:
      a wall having a first end and a second end separated by an expiratory limb length, the wall defining a lumen within and wherein at least a part of said wall comprises a breathable material configured to allow transmission of water vapor but substantially prevent a bulk flow of liquid water;
      a first opening defined by the first end of the wall, the first opening configured to receive a gas at a first temperature and a first relative humidity;
      a second opening defined by the second end of the wall, the second opening configured to allow the gas to exit the drying expiratory limb, the gas having a second temperature and a second relative humidity upon exiting the drying expiratory limb; and
      wherein the drying expiratory limb is configured such that a temperature of the gas has a temperature drop along the expiratory limb length, the temperature drop being controlled to reduce and/or prevent rain-out along the expiratory limb length by one or more of:
         a) an insulating material attached to an outer surface of the wall, the insulating material providing a varying insulation along the expiratory limb length;
         b) a heating element having a varying pitch spacing along the expiratory limb length; and
         c) at least two heating element sections along the expiratory limb length, each of the at least two heating element sections being independently controllable.

2. The breathing circuit of claim 1, wherein a first pitch spacing is positioned between the first opening and a second pitch spacing, and wherein the first pitch spacing is shorter than the second pitch spacing.

3. The breathing circuit of claim 1, wherein the insulating material has a first insulation portion and a second insulation portion, the first insulation portion having a different insulation value than the second insulation portion.

4. The breathing circuit of claim 3, wherein the first insulation portion comprises thicker insulation than the second insulation portion.

5. The breathing circuit of claim 1, wherein the drying expiratory limb is configured to control the temperature of the gas to be between about 0.9° C. and 1° C. above a dew point temperature of the gas along the expiratory limb length.

6. The breathing circuit of claim 1, wherein the drying expiratory limb is configured such that a rate of temperature decrease of the gas from the first end to a distance of about 300 mm from the first end is less than or equal to about −0.01° C./mm.

7. The breathing circuit of claim 1, further comprising a controller configured to provide heating control to the expiratory limb heating element.

8. The breathing circuit of claim 1, wherein the expiratory limb heating element comprises a first heater wire and a second heater wire, the first heater wire having the first winding density and the second heater wire having the second winding density.

9. The breathing circuit of claim 1, wherein a thickness of the insulating material is substantially constant along the expiratory limb length.

10. A breathing circuit comprising:
    an inspiratory limb comprising an inspiratory limb heating element that is configured to reduce condensation along the inspiratory limb or to control a temperature of gas arriving at a user or both; and
    a drying expiratory limb comprising:
       a wall having a first end and a second end separated by an expiratory limb length, the wall defining a lumen within and wherein at least a part of said wall comprises a breathable material configured to allow transmission of water vapor but substantially prevent a bulk flow of liquid water;
       a first opening defined by the first end of the wall, the first opening configured to receive a gas at a first temperature and a first relative humidity;
       a second opening defined by the second end of the wall, the second opening configured to allow the gas to exit the drying expiratory limb, the gas having a second temperature and a second relative humidity upon exiting the drying expiratory limb; and
       wherein the drying expiratory limb is configured such that a temperature of the gas has a temperature drop along the expiratory limb length, the temperature drop being controlled to reduce and/or prevent rain-out along the expiratory limb length by one or more of:
          a) an insulating material attached to an outer surface of the wall, the insulating material providing a varying insulation along the expiratory limb length;
          b) a heating element having a varying pitch spacing along the expiratory limb length; and
          c) at least two heating element sections along the expiratory limb length, each of the at least two heating element sections being independently controllable.

11. The breathing circuit of claim 10, wherein the drying expiratory limb is configured to limit a temperature drop rate of the gas to between about 0° C./mm and about −0.009° C./mm from the first end to about 300 mm from the first end.

12. The breathing circuit of claim 10, wherein the drying expiratory limb is configured to limit a temperature drop of the gas along the expiratory limb length to less than or equal to about 10° C.

13. The breathing circuit of claim 10, wherein the insulation material has a first insulation portion and a second insulation portion, the first insulation portion having a different insulation value than the second insulation portion.

14. The breathing circuit of claim 13, wherein the first insulation portion comprises thicker insulation material than the second insulation portion.

15. The breathing circuit of claim 10, wherein the drying expiratory limb is configured to control the temperature of the gas to be between about 0.9° C. and 1° C. above a dew point temperature of the gas along the expiratory limb length.

16. The breathing circuit of claim 10 wherein the expiratory limb heating element has a first section and a second section, the first section and the second section being independently controllable.

17. The breathing circuit of claim 16 further comprising a controller configured to independently provide heating control to the first section and the second section of the expiratory limb heating element.

18. The breathing circuit of claim 16, wherein the first section and the second section are spaced apart.

19. The breathing circuit of claim 16, wherein the first section and the second section are connected.

20. The breathing circuit of claim 10, wherein a thickness of the insulating material is substantially constant along the expiratory limb length.

21. The breathing circuit of claim 1 wherein the expiratory limb heating element has a first winding density and a second winding density, the first winding density being different than the second winding density.

22. The breathing circuit of claim 1, wherein a size of the insulating material is substantially constant along the expiratory limb length.

23. The breathing circuit of claim 10, wherein a size of the insulating material is substantially constant along the expiratory limb length.

* * * * *

UNITED STATES PATENT AND TRADEMARK OFFICE
CERTIFICATE OF CORRECTION

| | |
|---|---|
| PATENT NO. | : 11,413,418 B2 |
| APPLICATION NO. | : 16/668653 |
| DATED | : August 16, 2022 |
| INVENTOR(S) | : Robert Andrew David Milne et al. |

It is certified that error appears in the above-identified patent and that said Letters Patent is hereby corrected as shown below:

In the Specification

In Column 8, Line 59, before "FIGS. 29-33", delete "FIG. 15".

In Column 17, Line 26, before "FIGS.", delete "FIG. 11C or 11D".

In Column 17, Line 43, delete "FIG." and insert --FIGS.--.

In Column 17, Line 46, before "FIGS. 24A-25B", delete "FIG.".

In the Claims

In Column 21, Claim 13, Lines 5-6. delete "insulation" and insert --insulating--.

Signed and Sealed this
Twenty-third Day of January, 2024

Katherine Kelly Vidal
*Director of the United States Patent and Trademark Office*